United States Patent
Takahashi et al.

(10) Patent No.: US 8,859,852 B2
(45) Date of Patent: Oct. 14, 2014

(54) TRANSFORMATION OF A PLANT TO PROMOTE ROOT AND/OR LEAF GROWTH

(75) Inventors: Shinya Takahashi, Kanagawa (JP); Takanari Ichikawa, Kanagawa (JP); Minami Matsui, Kanagawa (JP); Tomoko Kuriyama, Kanagawa (JP); Yukako Hasegawa, Kanagawa (JP); Hirohiko Hirochika, Ibaraki (JP); Masaki Mori, Ibaraki (JP)

(73) Assignees: Riken, Wako-shi (JP); National Institute of Agrobiological Sciences, Tsukuba-shi (JP)

( * ) Notice: Subject to any disclaimer, the term of this patent is extended or adjusted under 35 U.S.C. 154(b) by 767 days.

(21) Appl. No.: 12/746,654

(22) PCT Filed: Dec. 5, 2008

(86) PCT No.: PCT/JP2008/072595
§ 371 (c)(1),
(2), (4) Date: Oct. 6, 2010

(87) PCT Pub. No.: WO2009/072676
PCT Pub. Date: Jun. 11, 2009

(65) Prior Publication Data
US 2011/0023189 A1    Jan. 27, 2011

(30) Foreign Application Priority Data
Dec. 6, 2007 (JP) ................................ 2007-315953

(51) Int. Cl.
*A01H 1/00* (2006.01)
*C12N 15/82* (2006.01)
*C12N 15/87* (2006.01)
*C07K 14/415* (2006.01)
*A01H 5/08* (2006.01)

(52) U.S. Cl.
CPC .......... *C12N 15/8261* (2013.01); *C07K 14/415* (2013.01); *C12N 15/8262* (2013.01); *A01H 5/0812* (2013.01)
USPC ........................................ 800/290; 435/468

(58) Field of Classification Search
USPC ....................................................... 800/290
See application file for complete search history.

(56) References Cited

U.S. PATENT DOCUMENTS

2006/0123505 A1* 6/2006 Kikuchi et al. ................ 800/278

FOREIGN PATENT DOCUMENTS

JP    2005 185101    7/2005

OTHER PUBLICATIONS

Guo et al., Protein tolerance to random amino acid change, 101 PNAS No. 25, 9205-9210 (2004).*
Matsuoka et al. (Expression of a Rice Homeobox Gene Causes Altered Morphology of Transgenic Plants, 5 Plant Cell, 1039-1048 (1993).*
Bevan and Walsh (The *Arabidopsis* genome: A foundation for plant research, 15 Genome Research, 1632-1642 (2005)).*
UniProtKB Accession No. Q61587 page, Version 34 published Dec. 4, 2007.*
Morita et al., Characterization of OsPID, the Rice ORtholog of PINOID, and its possible involvement in the control of polar auxin transport, 48 Plant Cell Phys. No. 3, 540-549 at 543 (2007); published online Feb. 7, 2007.*
Cheng et al., Calcium signaling through Protein Kinases. The *Arabidopsis* Calcium-dependent protein kinase gene family, 129 Plant Phys., 469-485 (2002).*
Extended European Search Report issued Jul. 6, 2011, in Patent Application No. 08857025.4.
Hajime Ohyanagi, et al., "The Rice Annotation Project Database (RAP-DB): hub for *Oryza sativa* ssp. japonica genome information", Nucleic Acids Research, vol. 34, XP009149384, Jan. 2006, Database issue pp. D741-D744.
Jun Yu, et al., "The Genomes of *Oryza sativa*: A History of Duplications", PLOS Biology, Public Library of Science, vol. 3, No. 2, XP008091831, Feb. 1, 2005, pp. 266-281.
Shoshi Kikuchi, et al., "Collection, Mapping, and Annotation of over 28,000 cDNA Clones from japonica Rice", vol. 301, No. 5631, XP008133546, Jul. 18, 2003, pp. 376-379.
Nakamura, Hidemitsu et al., "A genome-wide gain-of-function analysis of rice genes using the FOX-hunting system". Plant Mol , Biol., vol. 64, No. 4, pp. 357-351, (Nov. 2007).
Yang, Guangxiao et al., "A novel brassinolide-enhanced gene identified by cDNA microarray is involved in the growth of rice". Plant Molecular Biology, vol. 52, No. 4, pp. 843-854. (Jul. 2003).
Steele, K.A. et al., "Marker-assisted selection to introgress rice QTLs controlling root traits into an Indian upland rice variety", Theor Appl Genet, vol. 112 No. 2, pp. 208-221, (Jan. 2006).
International Search Report issued Jan. 20, 2009 in PCT/JP08/72595 filed Dec. 5, 2008.

* cited by examiner

*Primary Examiner* — Cynthia Collins
*Assistant Examiner* — Rebecca Coobs
(74) *Attorney, Agent, or Firm* — Oblon, Spivak, McClelland, Maier & Neustadt, L.L.P.

(57) ABSTRACT

The present invention is directed to identify genes involved in the growth of a plant and provide a transformed plant the growth of which is promoted utilizing the genes.

8 Claims, 4 Drawing Sheets

C

D

A

B

TRANSFORMATION OF A PLANT TO PROMOTE ROOT AND/OR LEAF GROWTH

This application is a National Stage of PCT/JP08/072,595 filed Dec. 5, 2008 and claims the benefit of JP 2007-315953 filed Dec. 6, 2007.

TECHNICAL FIELD

The present invention relates to a transformed plant the growth of which is promoted and a method for producing the plant.

BACKGROUND ART

Roots of a plant plays important roles, such as nutritional absorption and anchoring a plant body upright. However, many of the factors associated with such physiological phenomena remain unknown.

Recently, a method called FOX hunting system has been developed, by which genes whose DNA sequences have been determined but functions have not been understood yet can be comprehensively analyzed (JP Patent Publication No. 2003-018808 A). In this system, full-length cDNA is linked to a high-expression vector and the vector thus obtained is introduced into *Arabidopsis thaliana*, whereby *Arabidopsis thaliana* highly-expressing the full-length cDNA is produced. The FOX hunting system described as above is applicable to various genetic analyses.

On the other hand, some patent applications relating to the growth of a plant have been filed, and examples thereof include those relating to a gene-controlling extension of plant roots (JP Patent Publication No. 2004-187564 A), a method for promoting the growth of a plant (JP Patent Publication No. 2004-305051 A), and a method for increasing the growth of a plant and crop yield (JP Patent Publication No. 2002-531083 A). JP Patent Publication No. 2004-187564 A discloses that an *Arabidopsis thaliana* gene specifically expressed in root tips (AtGCN20-3) was identified utilizing *Arabidopsis thaliana* T-DNA tag lines. JP Patent Publication No. 2004-305051 A discloses that extension of growing organs such as roots is promoted by over-expression of a plant-derived cyclin B2 gene. JP Patent Publication No. 2002-531083 A discloses that a plant is transformed with a nucleic acid encoding a cyclin protein that is linked to regulatory sequences to produce a transformed plant exhibiting increased growths of roots and shoots.

DISCLOSURE OF THE INVENTION

The present invention is directed to identify genes involved in the growth of a plant, and to provide a transformed plant the growth of which is promoted utilizing the genes and a method for producing the plant.

The present inventors conducted a thorough research to achieve the aforementioned goal. As a result, we have produced *Arabidopsis thaliana* lines each highly-expressing one rice full-length cDNA (called rice FOX lines), and conducted a root bending assay to isolate *Arabidopsis thaliana* exhibiting changes in root extension in comparison with the wild-type plant, and sequenced the rice full-length cDNA introduced into the *Arabidopsis thaliana* thus isolated to identify DNA involved in the growth of a plant, thereby completing the present invention.

The present invention is summarized as follows.
[1] A transformed plant comprising DNA of any of the following (a) to (g) introduced thereinto:
(a) DNA comprising a nucleotide sequence of SEQ ID NO:1, SEQ ID NO:3, SEQ ID NO:5, or SEQ ID NO:7;
(b) DNA comprising a nucleotide sequence of SEQ ID NO:1, SEQ ID NO:3, SEQ ID NO:5, or SEQ ID NO:7 in which one or several nucleotides are deleted, substituted or added, and encoding a protein having an activity to promote the growth of a plant;
(c) DNA comprising a nucleotide sequence having a 90% or more identity to the nucleotide sequence of SEQ ID NO:1, SEQ ID NO:3, SEQ ID NO:5, or SEQ ID NO:7, and encoding a protein having an activity to promote the growth of a plant;
(d) DNA which hybridizes to DNA comprising a nucleotide sequence complementary to DNA comprising the nucleotide sequence of SEQ ID NO:1, SEQ ID NO:3, SEQ ID NO:5, or SEQ ID NO:7 under stringent conditions, and encodes a protein having an activity to promote the growth of a plant;
(e) DNA encoding a protein comprising an amino acid sequence of SEQ ID NO:2, SEQ ID NO:4, SEQ ID NO:6, or SEQ ID NO:8;
(f) DNA encoding a protein comprising an amino acid sequence of SEQ ID NO:2, SEQ ID NO:4, SEQ ID NO:6, or SEQ ID NO:8 in which one or several amino acids are deleted, substituted or added, and having an activity to promote the growth of a plant; and
(g) DNA encoding a protein comprising an amino acid sequence having a 90% or more identity to the amino acid sequence of SEQ ID NO:2, SEQ ID NO:4, SEQ ID NO:6, or SEQ ID NO:8, and having an activity to promote the growth of a plant.
[2] The transformed plant according to [1], wherein the activity to promote the growth of a plant is an activity to promote root extension.
[3] The transformed plant according to [1] or [2], wherein the activity to promote the growth of a plant is an activity to increase a leaf area.
[4] The transformed plant according to any of [1] to [3], being a monocotyledon or a dicotyledon.
[5] The transformed plant according to any of [1] to [4], being a plant body, a part of a plant body, a cultured plant cell, or a seed.
[6] A recombinant vector comprising DNA of any of the following (a) to (g):
(a) DNA comprising a nucleotide sequence of SEQ ID NO:1, SEQ ID NO:3, SEQ ID NO:5, or SEQ ID NO:7;
(b) DNA comprising a nucleotide sequence of SEQ ID NO:1, SEQ ID NO:3, SEQ ID NO:5, or SEQ ID NO:7 in which one or several nucleotides are deleted, substituted or added, and encoding a protein having an activity to promote the growth of a plant;
(c) DNA comprising a nucleotide sequence having a 90% or more identity to the nucleotide sequence of SEQ ID NO:1, SEQ ID NO:3, SEQ ID NO:5, or SEQ ID NO:7, and encoding a protein having an activity to promote the growth of a plant;
(d) DNA hybridizing to DNA comprising a nucleotide sequence complementary to DNA comprising the nucleotide sequence of SEQ ID NO:1, SEQ ID NO:3, SEQ ID NO:5, or SEQ ID NO:7 under stringent conditions, and encoding a protein having an activity to promote the growth of a plant;
(e) DNA encoding a protein comprising an amino acid sequence of SEQ ID NO:2, SEQ ID NO:4, SEQ ID NO:6, or SEQ ID NO:8; (0 DNA encoding a protein comprising an amino acid sequence of SEQ ID NO:2, SEQ ID NO:4, SEQ ID NO:6, or SEQ ID NO:8 in which one or several amino acids are deleted, substituted or added, and having an activity to promote the growth of a plant; and (g) DNA encoding a protein comprising an amino acid sequence having a 90% or more identity to the amino acid sequence of SEQ ID NO:2, SEQ ID NO:4, SEQ ID NO:6, or SEQ ID NO:8, and having an activity to promote the growth of a plant.

[7] A method for producing a transformed plant comprising introducing DNA of any of the following (a) to (g) into a plant cell and cultivating the plant:

(a) DNA comprising a nucleotide sequence of SEQ ID NO:1, SEQ ID NO:3, SEQ ID NO:5, or SEQ ID NO:7;

(b) DNA comprising a nucleotide sequence of SEQ ID NO:1, SEQ ID NO:3, SEQ ID NO:5, or SEQ ID NO:7 in which one or several nucleotides are deleted, substituted or added, and encoding a protein having an activity to promote the growth of a plant;

(c) DNA comprising a nucleotide sequence having a 90% or more identity to the nucleotide sequence of SEQ ID NO:1, SEQ ID NO:3, SEQ ID NO:5, or SEQ ID NO:7, and encoding a protein having an activity to promote the growth of a plant;

(d) DNA which hybridizes to DNA comprising a nucleotide sequence complementary to DNA comprising the nucleotide sequence of SEQ ID NO:1, SEQ ID NO:3, SEQ ID NO:5, or SEQ ID NO:7 under stringent conditions, and encodes a protein having an activity to promote the growth of a plant;

(e) DNA encoding a protein comprising an amino acid sequence of SEQ ID NO:2, SEQ ID NO:4, SEQ ID NO:6, or SEQ ID NO:8;

(f) DNA encoding a protein comprising an amino acid sequence of SEQ ID NO:2, SEQ ID NO:4, SEQ ID NO:6, or SEQ ID NO:8 in which one or several amino acids are deleted, substituted or added, and having an activity to promote the growth of a plant; and (g) DNA encoding a protein comprising an amino acid sequence having a 90% or more identity to the amino acid sequence of SEQ ID NO:2, SEQ ID NO:4, SEQ ID NO:6, or SEQ ID NO:8, and having an activity to promote the growth of a plant.

[8] The method according to [7], wherein the DNA is introduced using the recombinant vector according to [6].

The present specification encompasses the contents described in the specification and/or figures in JP Patent Application No. 2007-315953, based on which the present application claims a priority.

Figure 1:
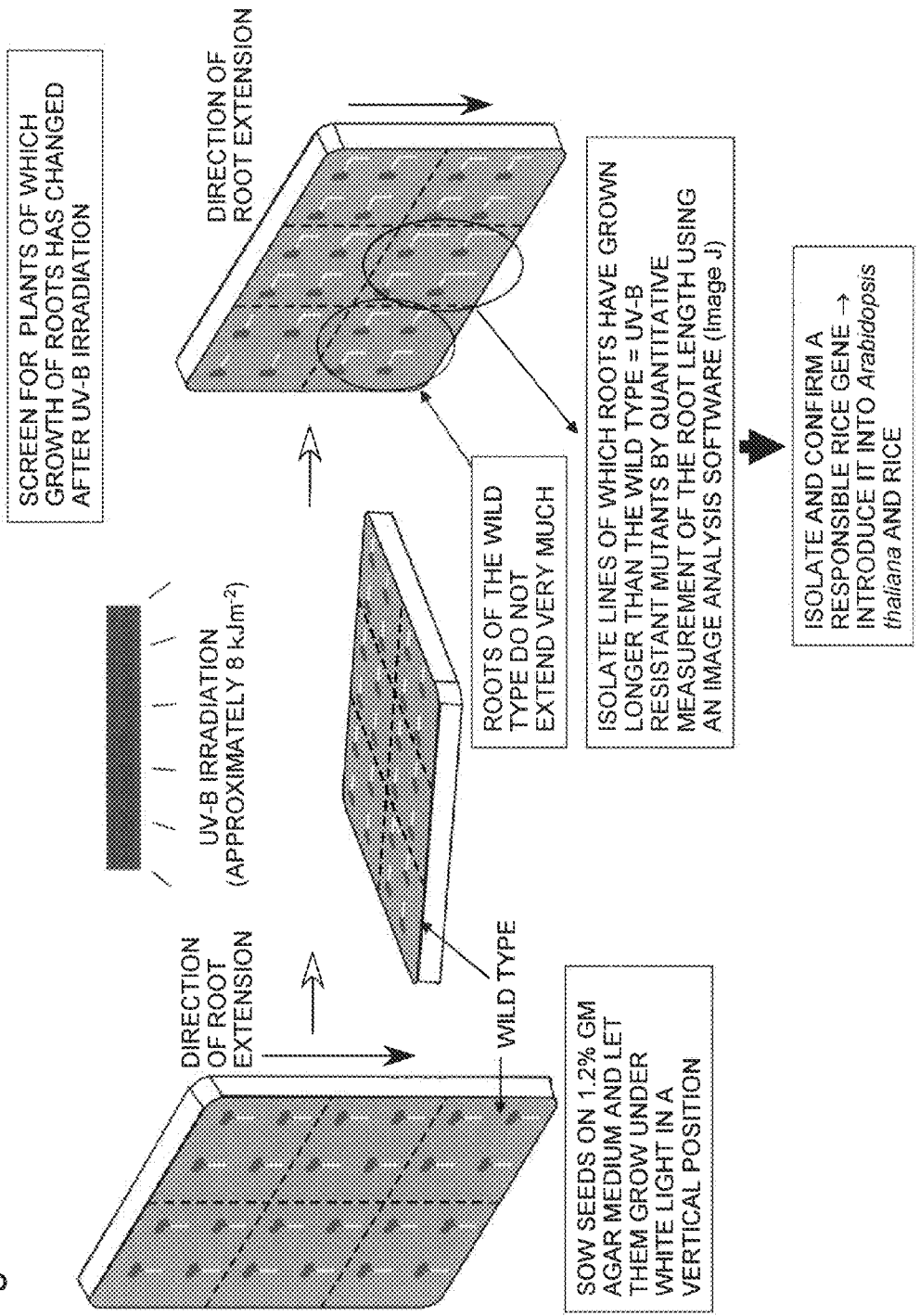
FIG. 1 shows an overview of a root bending assay.

BEST MODE FOR CARRYING OUT THE INVENTION (1) DNA Involved in Promotion of the Growth of a Plant DNA involved in promotion of the growth of a plant used in the present invention is DNA of SEQ ID NO:1, SEQ ID NO:3, SEQ ID NO:5, and SEQ ID NO:7, and amino acids encoded by the DNA are SEQ ID NO:2, SEQ ID NO:4, SEQ ID NO:6, and SEQ ID NO:8, respectively. The sequence information above has been reported to National Center for Biotechnology Information (NCBI). The NCBI accession numbers corresponding to SEQ ID NOs: 1 to 8 are shown below.

TABLE 1

| Rice FOX line | Accession No. |
| --- | --- |
| 1 (SEQ ID NOs: 1, 2) | AK069726 |
| 2 (SEQ ID NOs: 3, 4) | AK070346 |
| 3 (SEQ ID NOs: 5, 6) | AK067987 |
| 4 (SEQ ID NOs: 7, 8) | AK066897 |

The above-described DNA involved in promotion of the growth of a plant was found as a result of searching through rice genes using the FOX hunting system and the root bending assay.

The FOX hunting system (Full-length cDNA Over-expressor Gene Hunting System) is a method for elucidating the function of DNA based on changes in traits resulted from over-expression of full-length cDNA introduced into a plant (see JP Patent Publication No. 2003-018808 A). In the present invention, rice full-length cDNA was used as full-length cDNA to be introduced into a plant, and *Arabidopsis thaliana* was used as a plant into which full-length cDNA was to be introduced.

Specifically, approximately 13,000 rice full-length cDNAs are prepared as a pool having an equivalent ratio of the cDNAs (called normalization), and the cDNA is integrated into a T-DNA vector having a regulatory region such as a promoter, an enhancer, and a terminator, and a selection marker such as a drug-resistance gene. The resulted T-DNA vectors are introduced into *Agrobacterium*, whereby a rice full-length cDNA expression library (called a rice FOX library) is produced. *Arabidopsis thaliana* is transformed using the *Agrobacterium* by the floral dipping method to produce *Arabidopsis thaliana* transformant lines (rice FOX lines). In the FOX hunting system, because only one or two clones are introduced per plant even when plants are infected with a library consisting of hundreds of millions of clones, transformant lines in which each plant has different clone(s) introduced thereinto can be produced. T1 seeds are collected from the aforementioned transformed *Arabidopsis thaliana* and sown, and then seeds of T2 generation are collected. The T2 seeds are subjected to the root bending assay for screening.

The root bending assay is a method described in the article by Britt et al., (1993), A UV-sensitive mutant of *Arabidopsis* defective in the repair of pyrimidine-pyrimidinone (6-4) dimers. Science 261:, 1571-1574, which is carried out specifically as follows in the present invention.

T2 seeds of rice FOX lines and wild-type seeds are sown on MS agar media and subjected to a dark treatment and a vernalization treatment. Subsequently, the media are held vertically and the seeds are grown under continuous white light so that roots extend along the surface of the agar medium. Then, the agar medium are placed horizontally and irradiated with UV-B in the dark. Subsequently, the plates are held vertically and rotated by ninety degrees to change the direction of root extension, and the roots are again grown under continuous white light. Then, the lengths of the roots extended after irradiation with UV-B are compared between the wild-type plants and the T2 plants of the rice FOX lines, and the line that has extended the root longer than the wild type is isolated as a candidate UV-B-resistant line.

With regard to the candidate UV-B-resistant rice FOX line thus isolated, the introduced rice full-length cDNA is sequenced, and *Arabidopsis thaliana* is re-transformed with the rice full-length cDNA, and whether a phenotype exhibiting promoted root extension can be reproduced in the resulted re-transformed plant is verified (see FIG. 1).

The identified DNAs are, specifically, DNAs consisting of the nucleotide sequence of SEQ ID NO:1, SEQ ID NO:3, SEQ ID NO:5, and SEQ ID NO:7, respectively.

The aforementioned DNA encodes a protein having an activity to promote the growth of a plant. Herein, the "activity to promote the growth of a plant" is not particularly limited as long as it is an activity to promote the growth of a plant in comparison with the wild type, and examples thereof include an activity to promote root extension and/or an activity to increase a leaf area. The degree to which the growth of a plant is promoted is not limited as long as the growth of the plant is statistically significant compared to that of the wild type. For example, the length of the root of the transformed plant of the present invention is preferably 5% or more, 10% or more, 15% or more, 20% or more, 25% or more, 30% or more, 35% or more, 40% or more, 45% or more, and 50% or more longer than the length of the root of the wild type. Also, the leaf area of the transformed plant of the present invention is preferably 5% or more, 10% or more, 15% or more, 20% or more, 25% or more, 30% or more, 35% or more, 40% or more, 45% or more, and 50% or more larger than the leaf area of the wild type.

DNA to be used in the present invention can be DNA consisting of nucleotide sequences of the aforementioned SEQ ID NOs in which one or several nucleotides are deleted, substituted or added as long as the protein encoded by the DNA has an activity to promote the growth of a plant.

In the present specification, "a nucleotide sequence of SEQ ID NO:1 in which one or several nucleotides are deleted, substituted or added" means that, for example, one to 10 nucleotides, preferably one to five nucleotides can be deleted from the nucleotide sequence of SEQ ID NO:1, or one to 10 nucleotides, preferably one to five nucleotides can be added to the nucleotide sequence of SEQ ID NO:1, or one to 10 nucleotides, preferably one to five nucleotides in the nucleotide sequence of SEQ ID NO:1 can be substituted by other nucleotides.

Further, DNA to be used in the present invention can be DNA consisting of a nucleotide sequence having a 90% or more identity to the nucleotide sequences of the aforementioned SEQ ID NOs as long as the protein encoded by the DNA has an activity to promote the growth of a plant.

In the present specification, the "identity" in "a nucleotide sequence having a 90% or more identity to the nucleotide sequence of SEQ ID NO:1" is 90% or more, preferably 95% or more, more preferably 98% or more, and even more preferably 99% or more.

The "identity" of the nucleotide sequence as used herein means, in the alignment of two nucleotide sequences, the degree of coincidence between the sequences observed when the two sequences are aligned in such a way that the number of the identical nucleotides is maximized. Specifically, it is expressed as a percentage (%) of the number of the identical nucleotides with respect to the total number of nucleotides. The % identity can be determined using a known algorithm such as BLAST and FASTA. When gaps are introduced, for example, when using FASTA, the number of the gaps is also added on the total number of nucleotides.

Further, DNA to be used in the present invention can be DNA which hybridizes to DNA consisting of a nucleotide sequence complementary to DNA consisting of the nucleotide sequences of the aforementioned SEQ ID NOs under stringent conditions as long as the protein encoded by the DNA has an activity to promote the growth of a plant.

In the present specification, the "stringent conditions" refers to conditions under which a so-called specific hybrid is formed, while a non-specific hybrid is substantially not formed. Examples of such conditions include conditions under which a nucleic acid having a high identity, that is, a complementary strand of DNA consisting of a nucleotide sequence having a 90% or more, preferably a 95% or more, more preferably a 98% or more, and even more preferably a 99% or more identity to the nucleotide sequence of SEQ ID NO:1 hybridizes, while a complementary strand of a nucleic acid less identical than the above does not hybridize. More specifically, such conditions refers to conditions in which the sodium salt concentration is 15 to 750 mM, preferably 50 to 750 mM, and more preferably 300 to 750 mM, a temperature is 25 to 70° C., preferably 50 to 70° C., and more preferably 55 to 65° C., and the formamide concentration is 0 to 50%, preferably 20 to 50%, and more preferably 35 to 45%. Furthermore, under stringent conditions, conditions for washing a filter after hybridization are normally such that the sodium chloride concentration is 15 to 600 mM, preferably 50 to 600 mM, and more preferably 300 to 600 mM, and a temperature is 50 to 70° C., preferably 55 to 70° C., and more preferably 60 to 65° C.

Alternatively, the stringent conditions can be such conditions that hybridization is carried out in 2 to 6× sodium chloride/sodium citrate (SSC, 1×SSC contains 150 mM sodium chloride and 15 mM sodium citrate, and has a pH of 7.0) at room temperature to 40° C., and wash is carried out once or several times with 0.1 to 1×SSC (preferably 0.1 to 0.2×SSC) and 0.1% SDS at 50 to 68° C.

Further, DNA to be used in the present invention can be DNA encoding a protein consisting of the amino acid sequence of SEQ ID NO:2, SEQ ID NO:4, SEQ ID NO:6, or SEQ ID NO:8. The protein consisting of the amino acid sequence of SEQ ID NO:2, SEQ ID NO:4, SEQ ID NO:6, or SEQ ID NO:8 is encoded by DNA consisting of the nucleotide sequence of SEQ ID NO:1, SEQ ID NO:3, SEQ ID NO:5, or SEQ ID NO:7, respectively.

Further, DNA to be used in the present invention can be DNA encoding a protein consisting of amino acid sequences of the aforementioned SEQ ID NOs in which one or several amino acids are deleted, substituted or added as long as the protein encoded by the DNA has an activity to promote the growth of a plant.

Also, the amino acid sequence may contain conservative amino acid substitutions. Such substitutions occur, for example, between amino acids sharing a similar structural or electric property. The groups of such amino acids include (1) acidic amino acids: aspartic acid and glutamic acid; (2) basic amino acids: lysine, arginine, and histidine; (3) non-polar amino acids: alanine, valine, leucine, isoleucine, proline, phenylalanine, methionine, and tryptophan; (4) uncharged polar amino acids: glycine, asparagines, glutamine, cysteine, serine, threonine, and tyrosine; and (5) aromatic amino acids: phenylalanine, tyrosine, and tryptophan.

In the present specification, "an amino acid sequence of SEQ ID NO:2 in which one or several amino acids are deleted, substituted or added" means that, for example, one to 10 amino acids, preferably one to five amino acids can be deleted from the amino acid sequence of SEQ ID NO:2, or one to 10 amino acids, preferably one to five amino acids can be added to the amino acid sequence of SEQ ID NO:2, or one to 10 amino acids, preferably one to five amino acids in the amino acid sequence of SEQ ID NO:2 can be substituted by other amino acids.

Further, DNA to be used in the present invention can be DNA encoding a protein consisting of an amino acid sequence having a 90% or more identity to the amino acid sequences of the aforementioned SEQ ID NOs as long as the protein encoded by the DNA has an activity to promote the growth of a plant.

In the present specification, the "identity" in "an amino acid sequence having a 90% or more identity to the amino acid sequence of SEQ ID NO:2" is 90% or more, preferably 95% or more, more preferably 98% or more, and even more preferably 99% or more.

The "identity" of the amino acid sequence as used herein means, in the alignment of two amino acid sequences (or nucleotide sequences), the degree of coincidence between the sequences observed when the two sequences are aligned in such a way that the number of the identical amino acid residues is maximized. Specifically, it is expressed as a percentage (%) of the number of the identical amino acid residues with respect to the total number of amino acid residues. The % identity can be determined using a known algorithm such as BLAST and FASTA. When gaps are introduced, for example, when using FASTA, the number of the gaps is also added on the total number of amino acid residues.

DNA to be used in the present invention can be obtained as a nucleic acid fragment by PCR amplification using nucleic acids from a cDNA library or a genome DNA library and the like as a template with primers designed based on the sequence of any of SEQ ID NOs: 1 to 8. Also, the DNA can be obtained as a nucleic acid fragment by carrying out hybridization using nucleic acids from the aforementioned libraries and the like as a template, and employing a DNA fragment, which is a part of the DNA, as a probe. Alternatively, the DNA can be synthesized as a nucleic acid fragment by various nucleic acid sequence synthesis methods such as a chemical synthesis method known in the art.

Deletion, addition, and substitution of the aforementioned DNA or amino acids can be carried out by modifying DNA encoding the aforementioned protein with a technique known in the art. Introduction of mutations in DNA can be achieved by, for example, the Kunkel method or the Gapped duplex method, and mutations can be introduced using a mutation-introducing kit that utilizes a site-specific mutagenesis method (Mutan-K (Takara Bio Inc.) and a LA PCR in vitro mutagenesis kit (Takara Bio Inc.)) and the like.

The conventional technique such as the aforementioned PCR, hybridization, and recombination is described in, for example, Sambrook, J., et al. (1989), Molecular Cloning: Laboratory Manual, second edition, Cold Spring Harbor Laboratory Press, and Ausubel et al. (1995), Short Protocols In Molecular Biology, third edition, John Wiley & Sons, Inc.

(2) Recombinant Vector

The recombinant vector of the present invention to be used for transformation of a plant can be constructed by introducing DNA of any of (a) to (g) as described above into an appropriate vector. As the vector, pBI-based, pPZP-based, pSMA-based vectors and the like, which can allow introduction of target DNA into a plant via *Agrobacterium*, are preferably used. Particularly, a pBI-based binary vector or intermediate vector is preferably used, and examples thereof include pBI121, pBI101, pBI101.2, pBI101.3, and pBIG2113. A binary vector is a shuttle vector that is replicable in *Escherichia coli* and *Agrobacterium*. When a plant is infected with *Agrobacterium* containing a binary vector, DNA held between border sequences consisting of a LB sequence and a RB sequence on the vector is integrated into the nuclear DNA of the plant. Also, examples of other vectors include a pUC-based vector that can allow direct introduction of DNA into a plant such as pUC18, pUC19, and pUC9. Further, examples of other vectors include a plant virus vector such as cauliflower mosaic virus (CaMV), bean golden mosaic virus (BGMV), and tobacco mosaic virus (TMV).

When a binary vector-based plasmid is used, a target DNA is inserted between the border sequences (between LB and RB) of the aforementioned binary vector, and the recombinant vector thus obtained is multiplied in *E. coli*. Subsequently, the recombinant vectors thus multiplied are introduced into *Agrobacterium tumefaciens* GV3101, C58, LBA4404, EHA101, and EHA105, or *Agrobacterium rhizogenes* LBA1334, and the like, by electroporation and the like, and the target DNA is introduced into a plant using the *Agrobacterium* thus obtained.

In order to insert target DNA into a vector, a method in which purified DNA is cleaved by an appropriate restriction enzyme and then the resulting DNA is linked to a vector by inserting it into a restriction site or a multicloning site of the appropriate vector DNA, and the like, are applied.

Also, it is necessary to integrate target DNA into a vector in such a way that the DNA can exert its function. In this regard, a promoter, an enhancer, a terminator, an origin of replication required when using a binary vector-based plasmid (such as an origin of replication derived from a Ti or Ri plasmid), a selection marker gene, and the like can be linked to upstream, inside, or downstream of the target DNA.

The promoter is not necessary that from a plant as long as it is DNA that can function in a plant cell and induce an expression in a specific tissue or at a specific developmental stage of a plant. Specific examples thereof include cauliflower mosaic virus (CaMV) 35S promoter, a promoter of nopaline-synthase gene, ubiquitin promoter from corn, actin promoter from rice, and PR protein promoter from tobacco.

Examples of the enhancer include an enhancer region containing an upstream sequence of CaMV 35S promoter, a transcription enhancer E12, and an omega sequence, all of which are used to increase expression efficiency of target DNA.

The terminator may be a sequence that can terminate DNA transcription driven by the promoter, and examples thereof include a terminator of nopaline-synthase (NOS) gene, a terminator of octopine-synthase (OCS) gene, and a terminator of CaMV 35S RNA gene.

Examples of the selection marker gene include a hygromycin resistance gene, an ampicillin resistance gene, a neomycin resistance gene, a bialaphos resistance gene, and a dihydrofolate reductase gene.

(3) Transformed Plant and Method for Producing the Plant

The transformed plant of the present invention can be produced by introducing DNA of any of (a) to (g) as described above or the aforementioned recombinant vector into a target plant. In the present invention, "introduction of DNA" means that target DNA is introduced in the aforementioned host plant cell by, for example, a known genetic engineering method in such a way that the DNA can be expressed. The DNA thus introduced can be integrated into a host plant genome DNA or present as being contained within an exogenous vector.

Introduction of DNA or a recombinant vector may be carried out by a known method, and examples thereof include an

*Agrobacterium* method, a PEG-calcium phosphate method, electroporation, a particle gun method, and a microinjection method. The *Agrobacterium* method includes a method using a protoplast, a method using a piece of tissue, and a method using a whole plant (in planta method). The method using a protoplast can be carried out by a method in which a protoplast is co-cultured with *Agrobacterium* containing a Ti plasmid or a Ri plasmid (*Agrobacterium tumefaciens* or *Agrobacterium rhizogenes*, respectively) and a method in which a protoplast is fused with a spheroplast of *Agrobacterium* (a spheroplast method). The method using a piece of tissue can be carried out by a method in which steriled cultured leaf discs of a target plant are infected, or by infecting calluses (undifferentiated cultured cells), and the like. Also, the in planta method using a seed or a plant body is feasible by directly treating an imbibed seed, a young plant (young seedling), a potted plant, and the like with *Agrobacterium*. The aforementioned plant transformation methods can be carried out according to the description in "Shinpan Model shokubutu no jikken protocol, Idengakutekishuho kara genome kaiseki made (literal translation: New edition Experimental protocol for model plant, From genetic technique to genome analysis) (Supervised by SHIMAMOTO, Ko and OKADA, Kiyotaka, Shujunsha Co., Ltd., 2001)" and the like.

Whether the DNA is integrated into the plant body can be confirmed by PCR, Southern hybridization, Northern hybridization, and the like. For example, DNA is prepared from the transformed plant, and primers specific to the target DNA are designed, and PCR is carried out. Subsequently, the amplified product is subjected to agarose electrophoresis, polyacrylamide gel electrophoresis, or capillary electrophoresis, and then stained with ethidium bromide, SYBR Green solution, and the like so that the amplified product is detected as a single band, whereby transformation can be confirmed. Also, PCR can be carried out using a primer that is labeled with a fluorescent dye and the like in advance, and then the amplified product can be detected. Further, transformation may also be confirmed by a method in which the amplified product is bound to a solid phase such as a microplate, which is then confirmed by fluorescence or an enzymatic reaction, and the like.

Alternatively, transformation can also be confirmed by producing a vector having various reporter genes, for example, a gene of β-glucuronidase (GUS), luciferase (LUC), green fluorescent protein (GFP), chloramphenicol acetyltransferase (CAT), β-galactosidase (LacZ), and the like, linked to downstream of the target DNA, and transforming a plant using *Agrobacterium* having the vector introduced thereinto as described above, and then measuring the expression of the reporter gene.

A plant to be used for transformation in the present invention can be either a monocotyledon or a dicotyledon, and examples thereof include, but are not limited to, a plant belonging to the family Brassicaceae (including *Arabidopsis thaliana*, cabbage, and rapeseed), the family Poaceae (including rice, corn, barley, and wheat), and the family Solanaceae (including eggplant, tobacco, tomato, and potato).

In the present invention, a plant material to be subjected to transformation may be any of plant organ and tissue such as a stem, a leaf, a seed, an embryo, an ovule, an ovary, a shoot apex, an anther, and pollen, a section of the above plant organ and tissue, an undifferentiated callus, and a cultured plant cell such as a protoplast obtainable by removing a cell wall of the callus by an enzymatic treatment. Also, when the in planta method is used, an imbibed seed and an entire plant body can be used.

When a cultured plant cell is subjected to transformation, in order to regenerate a transformant from the resulted transformed cell, an organ or an organism may be regenerated by a known tissue culture method. A person skilled in the art can easily perform the regeneration as described above using a well-known method for regenerating a plant body from a plant cell. For example, regeneration of a plant body from a plant cell can be performed as follows.

When a plant tissue or a protoplast is used as a plant material to be subjected to transformation, the plant material or the protoplast is cultured in a callus-forming medium, which is prepared by adding inorganic elements, vitamins, carbon sources, sugars as an energy source, plant growth-regulating substances (plant hormones such as auxin, cytokinin, gibberellin, abscisic acid, ethylene, and brassinosteroid), followed by sterilization. The plant tissue or the protoplast is then allowed to form a dedifferentiated callus, which will proliferate into an amorphous mass (hereinafter called "callus induction"). The callus thus formed is transferred to a new medium containing plant growth-regulating substances such as auxin and allowed to further proliferate (subculture).

When the callus induction is performed on a solid medium such as agar and subculture is performed by, for example, liquid culture, each culture can be efficiently carried out in a large amount. Then, the callus proliferated by subculturing is cultured under appropriate conditions to induce re-differentiation of an organ (hereinafter called "re-differentiation induction"), and finally a complete plant body is regenerated. The re-differentiation induction can be carried out by appropriately setting composition of constituents in the medium such as plant growth-regulating substances including auxin and carbon sources, the amounts thereof, light, temperature, and the like. An adventitious embryo, an adventitious root, an adventitious shoot, an adventitious stem, an adventitious leaf, and the like are formed and these adventitious organs are grown into a complete plant body by the aforementioned re-differentiation induction. Alternatively, these adventitious organs can be stored until they grow into a complete plant body (for example, in the form of capsulated artificial seed, dried embryo, and lyophilized cell and tissue).

The transformed plant of the present invention encompasses any of an entire plant body, a part of a plant body (for example, a leaf, a petal, a stem, a root, and pollen), a cultured plant cell (for example, a callus and a protoplast), and a seed, having DNA of any of (a) to (g) as described above introduced thereinto. Further, it also encompasses a progeny plant body obtained by sexual or asexual reproduction of the plant body, a part, a cultured cell, and a seed of the progeny plant body. The transformed plant of the present invention can be mass-produced by obtaining a reproductive material such as a seed and a protoplast from the transformed plant and cultivating or culturing the reproductive material.

The growth of the transformed plant obtained as above, particularly root extension and/or an increase in the leaf area are promoted by overexpression of DNA of any of (a) to (g) as described above. As a result, the root will extend under the ground, whereby lodging resistance and drought resistance can be increased and cultivation of the plant in poor nutrition becomes possible. Further, because the growth of leafs is also promoted and a photosynthetic activity is facilitated, ultimately the growth of an entire plant can be promoted.

EXAMPLE 1

The present invention is further specifically described hereinbelow based on Examples; however, the present invention is not limited to these Examples.

(1) Production of Rice FOX Line by FOX Hunting System

In the present Example, rice full-length cDNA was screened using pBIG2113SF, which was obtained by introducing an SfiI cloning site into a constitutive expression vector, pBIG2113N (Taji, T. et al., Plant J., 2002. 24(4): p.p. 417-426 and Becker, D. et al., Nucleic Acid Res., 1990. 18(1): p. 203).

(i) Production of Normalized Rice Full-Length cDNA Mix

Full-length cDNA was prepared from rice by the CAP trapper method. The resulted cDNA was cloned into a site between SfiI restriction sites in Lambda ZAP or Lambda pLC-1-B (reference: Seki M. et al. Plant J., 15, 707-720 (1998)). Sequences at the 5' end and 3' end were sequenced using the vector sequence and cDNAs were grouped, and 20,000 independent clones were identified (reference: Seki M. et al. Plant Physiol. Biochem. 39, 211-220 (2001)). Subsequently, 0.5 µl aliquot from each clone prepared at 50 ng/µl was removed, and all the aliquots were mixed in a single tube. From the mixture, 1 µl aliquot was removed, with which 20 µl of the electric competent cell, DH10B (Gibco BRL), were transformed. Then, approximately 200,000 independent colonies grown on agar media containing Amp were mixed, from which plasmids were collected. The plasmids thus obtained were provided as a normalized rice full-length cDNA mix.

(ii) Production of Rice FOX Library

The normalized rice full-length cDNA mix (2 µg) and 700 µg of pBIG2113SF were mixed and simultaneously completely cleaved by SfiI. After cleavage, the cleaved products were concentrated by isopropanol precipitation. The concentrated products were dissolved in 8 µl of water, into which 1 µl of 10× buffer and 1 µl of T4 ligase were mixed, and a reaction was allowed to proceed for one full day at 16° C. The reaction solution (2 µl) was mixed with 40 µl of the electric competent cell, DH10B, and transformation is performed.

Then, approximately 150,000 independent colonies grown on agar media containing kanamycin (Km) were mixed, from which plasmids were collected. The plasmid solution thus collected (2 µl) was mixed with 40 µl of the electric competent *Agrobacterium* cell, GV3101, and transformation is performed. Approximately 150,000 independent colonies grown on agar media containing Km were suspended in LB liquid medium, to which glycerol was added to prepare a 15% glycerol solution, which was stored at −80° C. The glycerol solution thus obtained was provided as a rice FOX library.

(iii) Production of Rice FOX Lines

Approximately 200,000 colonies of the aforementioned rice FOX library were grown and suspended in a dipping solution, with which the floral dipping of the wild type *Arabidopsis thaliana* (ecotype: Colombia) was performed. Seeds (T1 seeds) were harvested and allowed to germinate on nutrient-poor media, BAM, containing hygromycin and then, only plants exhibiting hygromycin resistance (approximately 23,000 lines) were transplanted to soil.

(2) Screening of T2 Generation of Rice FOX Line by Root Bending Assay

Seeds (T2 seeds) were collected from the plants transplanted to soil in (1) (iii) above. The T2 seeds and the wild-type seeds were sterilized and sown on 1.2% agar media (MS medium containing vitamin B5). Then, the seeds were subjected to a dark treatment by wrapping the media with aluminum foils, and then to a vernalization treatment by placing the media at 4° C. for approximately one week. Subsequently, the media were held vertically so that roots would extend along the surface of the agar media, and the seeds were grown at 22° C. for three days under continuous white light. The agar media containing grown roots were placed horizontally, which were then irradiated with approximately 2.3 Wm$^{-2}$ of UV-B (approximately 8 kJm$^{-2}$) in the dark. Subsequently, the plates were held vertically and rotated by ninety degrees to change the direction of root extension, and the roots were again grown at 22° C. under continuous white light for three days (FIG. 1).

The lengths of the roots extended for three days after UV-B irradiation were evaluated. The UV-B resistance was judged by quantitatively measuring the root length using an image analysis software (Image J, National Institute for Health, USA). As a result, 49 lines were isolated from 7034 rice FOX lines subjected to the root bending assay as candidate UV-B resistant lines.

(3) Re-Cloning of cDNA and Sequencing of Rice Full-Length cDNA Inserted into Rice FOX Line Approximately two rosette leaves (approximately 200 mgfw) were collected from each of the candidate rice FOX lines selected in (2) above, from which genomic DNA was extracted. A PCR reaction was carried out on the DNA. The composition of the PCR reaction solution was as shown below, and the reaction conditions were as follows; 40 cycles of 94° C. for 0.5 minute, 55° C. for 0.5 minute, and 72° C. for four minutes.

Composition of the reaction solution:

| Primers (100 pM) | 2 × 0.25 µl |
|---|---|
| dNTP (200 µM) | 4 µl |
| Buffer (×2) | 25 µl |
| Polymerase | 0.5 µl |
| Genomic DNA | 10 µl |
| Distilled water | 10 µl |
| Total | 50 µl |

The primers used for PCR were as follows:

```
GTACGTATTTTTACAACAATTACCAACAAC    (SEQ ID NO: 9)

GGATTCAATCTTAAGAAACTTTATTGCCAA    (SEQ ID NO: 10)
```

The PCR products were collected from agarose gels, and then mixed with pBIG2113SF. The resultant was completely cleaved by SfiI and then precipitated by isopropanol, followed by treatment with T4 ligase. Then, *E. coli* was transformed with the resulted mixture. Plasmids into which the PCR fragments were inserted were selected and the nucleotide sequences of the inserted cDNA fragments were identified using the aforementioned primers.

(4) Confirmation of Phenotype of Promoted Root Extension

T2 seeds of *Arabidopsis thaliana* transformants into which the rice full-length cDNAs obtained in (3) above were re-introduced and the wild-type seeds, each approximately 20 seeds, were sterilized and sown on 1.2% agar media. Then, the seeds were subjected to a dark treatment by wrapping the media with aluminum foils, and then to a vernalization treatment by placing the media at 4° C. for approximately one week. Subsequently, the media were held vertically so that roots would extend along the surface of the agar media, and the seeds were grown at 22° C. for seven days under continuous white light. Subsequently, images of the plant bodies were taken and the lengths from the boundary between the hypocotyls and the roots to the root tips were measured by the aforementioned image analysis software.

The phenotype of promoted root extension was reproduced in the re-transformants. The images and plots of the root lengths of rice FOX lines 1 to 4 are shown in FIGS. 2 and 3.

Figure 2:
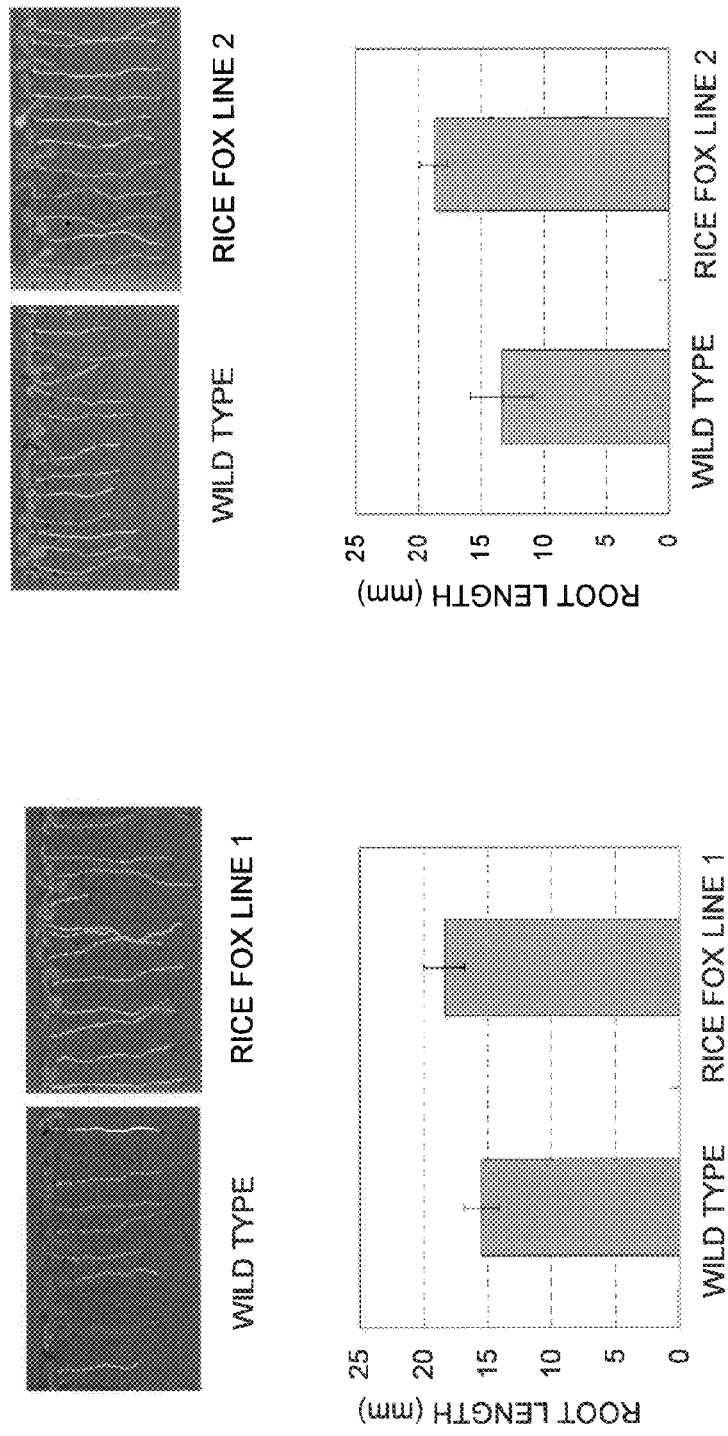
FIG. 2 shows extension of the roots of re-transformed rice FOX lines. Panel A shows rice FOX line 1 (SEQ ID NOs: 1 and 2), and panel B shows rice FOX line 2 (SEQ ID NOs: 3 and 4).
Figure 3:
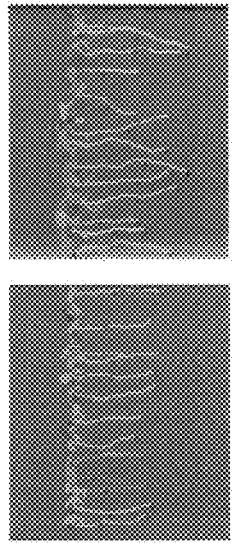
FIG. 3 shows extension of the roots of re-transformed rice FOX lines. Panel C shows rice FOX line 3 (SEQ ID NOs: 5 and 6), and panel D shows rice FOX line 4 (SEQ ID NOs: 7 and 8).
Figure 3:
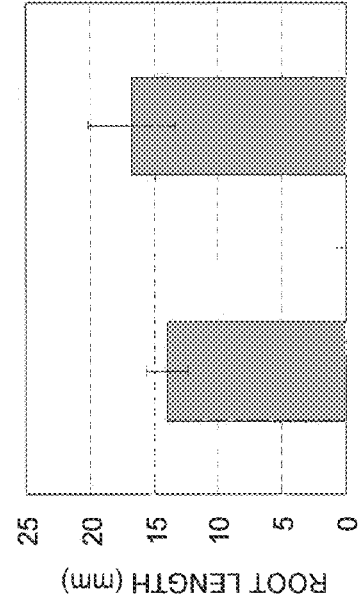
Figure 3:
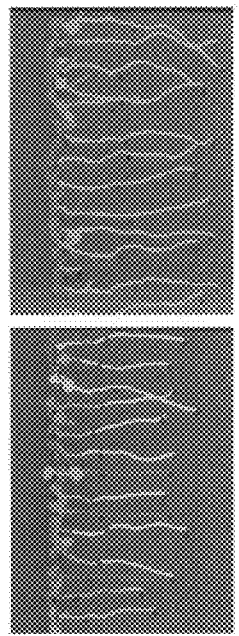
Figure 3:
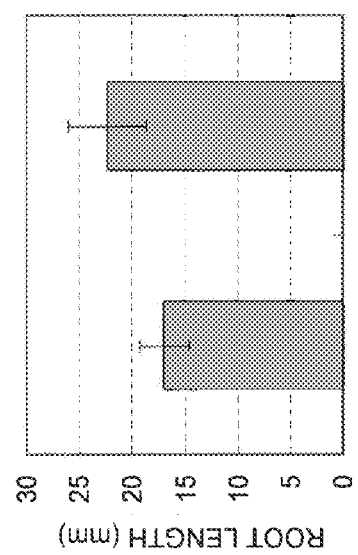

In panel A of FIG. 2, the root length of the wild type was 15.49 mm (average), while that of rice FOX line 1 was 18.36 mm (average). In panel B of FIG. 2, the root length of the wild type was 13.37 mm (average), while that of rice FOX line 2 was 18.76 mm (average). In panel C of FIG. 3, the root length of the wild type was 16.98 mm (average), while that of rice FOX line 3 was 22.25 mm (average). In panel D of FIG. 3, the root length of the wild type was 13.97 mm (average), while that of rice FOX line 4 was 16.78 mm (average).

The sequences of the rice full-length cDNA introduced into the aforementioned rice FOX lines are of SEQ ID NO:1, SEQ ID NO:3, SEQ ID NO:5, and SEQ ID NO:7, and the amino acid sequences are of SEQ ID NO:2, SEQ ID NO:4, SEQ ID NO:6, and SEQ ID NO:8.

(5) Confirmation of Phenotype of Increased Leaf Area

T2 seeds of *Arabidopsis thaliana* transformants into which the rice full-length cDNAs obtained in (3) above were re-introduced and the wild-type seeds, each 20 to 30 seeds, were sown in agricultural soil and subjected to a vernalization treatment by being placed at 4° C. for four days. Then, the seeds were cultivated at 22° C. with a 16-hour light period. On day 15 after initiation of cultivation under the light condition, images of the plant bodies were taken and the leaf areas were measured by the aforementioned image analysis software.

Figure 4:
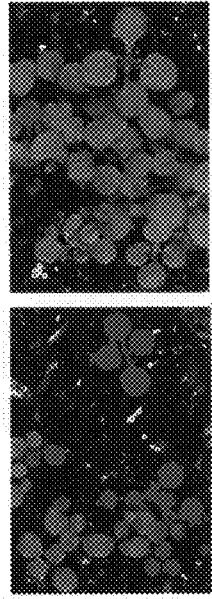
FIG. 4 shows increases in the leaf areas of re-transformed rice FOX lines. Panel A shows rice FOX line 1 (SEQ ID NOs: 1 and 2), and panel B shows rice FOX line 2 (SEQ ID NOs: 3 and 4).
Figure 4:
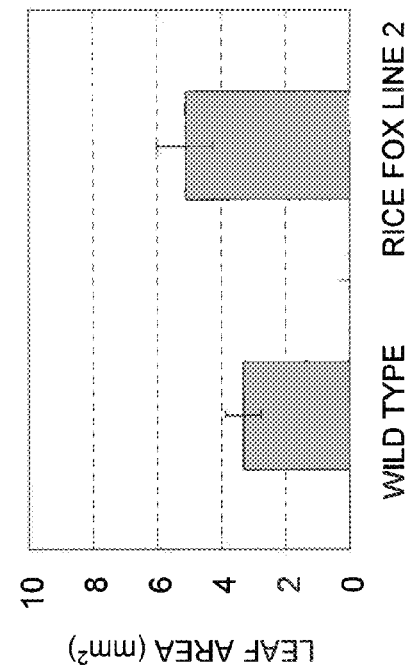
Figure 4:
Figure 4:
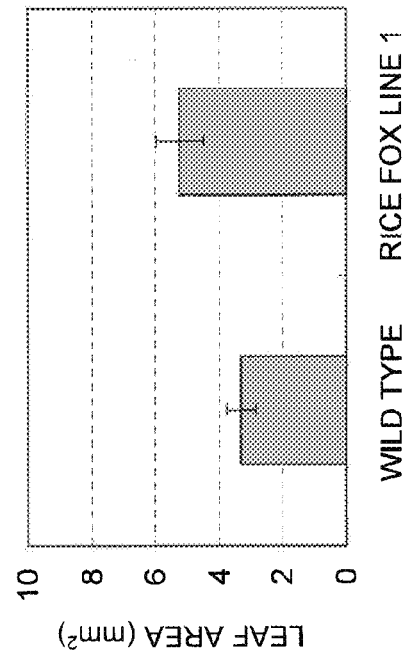

The phenotype of increased leaf area was reproduced in the re-transformants. The images and plots of the leaf areas of rice FOX lines 1 and 2 are shown in FIG. 4. In panel A of FIG. 4, the leaf area of the wild type was 3.30 mm$^2$ (average), while that of rice FOX line 1 was 5.22 mm$^2$ (average). In panel B of FIG. 4, the leaf area of the wild type was 3.31 mm$^2$ (average), while that of rice FOX line 2 was 5.11 mm$^2$ (average).

INDUSTRIAL APPLICABILITY

The genes whose function was elucidated according to the present invention are involved in the growth of a plant, particularly root extension. The nutrition-absorption ability of a plant is increased by overexpression of the genes in the plant enabling cultivation of a plant under poor nutritional conditions, and lodging resistance and drought resistance can be increased. Particularly, by enlarging edible parts of agricultural products whose main part is the root, such as root vegetables, a commercial value as an edible crop can be increased in the agricultural products.

Further, the genes are also involved in an increase in the leaf area. Overexpression of the genes in a plant can promote the growth above the ground. Particularly, by increasing edible parts of leaf vegetables by increasing the tissue amount above the ground, a commercial value as edible plants can be increased in the leaf vegetables.

As shown above, overexpression of the genes involved in root extension and an increase in the leaf area by transformation can ultimately produce plants the growth of which is entirely promoted. The present invention is applicable to any plants for which the transformation technique has been established.

All the publications, patents, and patent applications cited in the present specification are incorporated herein by reference in their entirety.

The invention claimed is:

1. A method for promoting growth of at least one of a plant root and a plant leaf, the method comprising introducing DNA comprising SEQ ID NO:3;

DNA having at least 95% identity to the full length nucleotide sequence of SEQ ID NO:3;

DNA encoding a protein comprising SEQ ID NO:4; or

DNA encoding a protein that is at least 95% identical to SEQ ID NO: 4 into a plant cell;

cultivating the plant cell to produce a plant with promoted growth of at least one of the root and the leaf of the plant; and selecting the plant with promoted growth of at least one of the root and the leaf of the plant.

2. The method according to claim 1, wherein the DNA is introduced using a recombinant vector.

3. The method according to claim 1, wherein the plant is a monocot or a dicot.

4. The method according to claim 1, wherein the DNA comprising SEQ ID NO:3 is introduced into the plant cell.

5. The method according to claim 1, wherein the DNA that is at least 95% identical to SEQ ID NO:3 is introduced into the plant cell.

6. The method according to claim 1, wherein the DNA encoding the protein comprising SEQ ID NO:4 is introduced into the plant cell.

7. The method according to claim 1, wherein the DNA encoding the protein that is at least 95% identical to SEQ ID NO:4 is introduced into the plant cell.

8. The method according to claim 1, wherein the plant is *Arabidopsis thaliana*.

* * * * *

SEQUENCE LISTING

```
<160> NUMBER OF SEQ ID NOS: 10

<210> SEQ ID NO 1
<211> LENGTH: 1894
<212> TYPE: DNA
<213> ORGANISM: Oryza sativa

<400> SEQUENCE: 1
gaagttgcaa cctcccgcct cacccgccgc cattgacgac caccgcgctc gtcccatccc      60
atgcctgcgg ccgtgaccgc gaggttgtga ggagaagaga gtcccaagag aggaggatcg     120
atgcggcagc ggcaggccgg cgagcaggag gcggagctgt tcgtccagtg gaggccctgc     180
gacaagaagc ggtcctagtc gcccgccgcc gctcgccac tcgccggcgt cgtcgatctg      240
agagggacag gggaagagga agaagcagag gaggaggagg atgagcgtgt cgggcgggag     300
gacgcgggtg gggaggtacg agctcgggag gacgctcggc gagggcacct tcgccaaggt     360
caagttcgcc cgcaacgcgg actccggcga gaatgtcgcc atcaagatcc tcgacaagga     420
caaggtcctc aagcacaaga tgatcgccca gataaagcgc gagatctcca ccatgaagct     480
catcaggcac cccaacgtca tccggatgca tgaggtgatg gccagcaaga ccaaaatata     540
catagtgatg gagcttgtca ccggtggtga acttttcgac aagattgctt cgcgtgggag     600
gctgaaagag gatgatgcaa ggaagtattt tccgcagctg atcaacgctg tcgattactg     660
tcatagcaga ggagtctatc accgggatct caagcccgaa aatcttctgc ttgatgctag     720
tggcactctc aaagtatcag attttgggct gagtgcactg tctcaacaag tcagagagga     780
tggtctgttg cacactacct gtggaactcc taattatgtt gctcccgagg ttatcaacaa     840
caaaggatat gatggagcca aggctgatct gtggtcatgt ggagtgattc tctttgtcct     900
catggcaggc taccttccat ttgaagactc aaacctcatg tcactttaca agaagatctt     960
```

-continued

```
caaagcagac ttcagttgcc cgtcttggtt ctctacaagt gcgaagaagc tcatcaagaa    1020
aatactagat cctaatccta gcaccaggat taccatcgca gagcttatca acaatgagtg    1080
gttcaagaag ggatatcagc ctccaaggtt tgagacagca gatgttaacc tggatgatat    1140
caactctatt tttaatgaat ctggggacca aacacagctt gttgtcgaga ggcgagaaga    1200
gaggccatca gtgatgaatg cttttgagtt gatctctaca tctcagggtc tcaatcttgg    1260
cacactcttt gaaaagcaat cgcagggttc tgtgaagcga aaacaagat ttgcatcaag     1320 gctgcctgca aacgagatat tgtcgaaaat tgaagcagct gctggaccca tgggctttaa    1380
tgtacagaag cgcaactaca agctgaagtt gcaaggagag aatccaggaa ggaaaggtca    1440
gcttgcaatt gcaacagagg ttttgaagt cacgccctcg ctgtacatgg ttgagctccg     1500
caaatctaac ggcgacactc ttgaattcca taagttctac cacaacatct ccaatggcct    1560
gaaagatgtg atgtggaagc cggagagtag cataatcgca ggcgatgaga tccagcatcg    1620
gaggtcaccg tgattggcag tttggcacca aaagttcagt gatagtataa ggtagataac    1680
cagccaggaa aacctactaa ggaatggcct gtggctgttt ttttttttttt tggttctttt   1740 taccttttaa gttgagttac tatctaatct agacatggt gtaaacaaag tttgtatgga     1800
gatggaatgt gaatgaagaa tgtgcatagt tttgcttcct tgacttattt taaaagcagt    1860
aacctgtgaa atccgatgaa tgaaattgaa atcg                                1894
```

<210> SEQ ID NO 2
<211> LENGTH: 450
<212> TYPE: PRT
<213> ORGANISM: Oryza sativa

<400> SEQUENCE: 2

```
Met Ser Val Ser Gly Gly Arg Thr Arg Val Gly Arg Tyr Glu Leu Gly
1               5                   10                  15

Arg Thr Leu Gly Glu Gly Thr Phe Ala Lys Val Lys Phe Ala Arg Asn
            20                  25                  30

Ala Asp Ser Gly Glu Asn Val Ala Ile Lys Ile Leu Asp Lys Asp Lys
        35                  40                  45

Val Leu Lys His Lys Met Ile Ala Gln Ile Lys Arg Glu Ile Ser Thr
    50                  55                  60

Met Lys Leu Ile Arg His Pro Asn Val Ile Arg Met His Glu Val Met
65                  70                  75                  80

Ala Ser Lys Thr Lys Ile Tyr Ile Val Met Glu Leu Val Thr Gly Gly
                85                  90                  95

Glu Leu Phe Asp Lys Ile Ala Ser Arg Gly Arg Leu Lys Glu Asp Asp
            100                 105                 110

Ala Arg Lys Tyr Phe Pro Gln Leu Ile Asn Ala Val Asp Tyr Cys His
        115                 120                 125

Ser Arg Gly Val Tyr His Arg Asp Leu Lys Pro Glu Asn Leu Leu Leu
    130                 135                 140

Asp Ala Ser Gly Thr Leu Lys Val Ser Asp Phe Gly Leu Ser Ala Leu
145                 150                 155                 160

Ser Gln Gln Val Arg Glu Asp Gly Leu Leu His Thr Thr Cys Gly Thr
                165                 170                 175

Pro Asn Tyr Val Ala Pro Glu Val Ile Asn Asn Lys Gly Tyr Asp Gly
            180                 185                 190

Ala Lys Ala Asp Leu Trp Ser Cys Gly Val Ile Leu Phe Val Leu Met
        195                 200                 205
```

```
Ala Gly Tyr Leu Pro Phe Glu Asp Ser Asn Leu Met Ser Leu Tyr Lys
    210                 215                 220

Lys Ile Phe Lys Ala Asp Phe Ser Cys Pro Ser Trp Phe Ser Thr Ser
225                 230                 235                 240

Ala Lys Lys Leu Ile Lys Lys Ile Leu Asp Pro Asn Pro Ser Thr Arg
                245                 250                 255

Ile Thr Ile Ala Glu Leu Ile Asn Asn Glu Trp Phe Lys Lys Gly Tyr
            260                 265                 270

Gln Pro Pro Arg Phe Glu Thr Ala Asp Val Asn Leu Asp Asp Ile Asn
        275                 280                 285

Ser Ile Phe Asn Glu Ser Gly Asp Gln Thr Gln Leu Val Val Glu Arg
    290                 295                 300

Arg Glu Glu Arg Pro Ser Val Met Asn Ala Phe Glu Leu Ile Ser Thr
305                 310                 315                 320

Ser Gln Gly Leu Asn Leu Gly Thr Leu Phe Glu Lys Gln Ser Gln Gly
                325                 330                 335

Ser Val Lys Arg Glu Thr Arg Phe Ala Ser Arg Leu Pro Ala Asn Glu
            340                 345                 350

Ile Leu Ser Lys Ile Glu Ala Ala Ala Gly Pro Met Gly Phe Asn Val
        355                 360                 365

Gln Lys Arg Asn Tyr Lys Leu Lys Leu Gln Gly Glu Asn Pro Gly Arg
    370                 375                 380

Lys Gly Gln Leu Ala Ile Ala Thr Glu Val Phe Glu Val Thr Pro Ser
385                 390                 395                 400

Leu Tyr Met Val Glu Leu Arg Lys Ser Asn Gly Asp Thr Leu Glu Phe
                405                 410                 415

His Lys Phe Tyr His Asn Ile Ser Asn Gly Leu Lys Asp Val Met Trp
            420                 425                 430

Lys Pro Glu Ser Ser Ile Ile Ala Gly Asp Glu Ile Gln His Arg Arg
        435                 440                 445

Ser Pro
    450

<210> SEQ ID NO 3
<211> LENGTH: 1937
<212> TYPE: DNA
<213> ORGANISM: Oryza sativa

<400> SEQUENCE: 3
ggatgggcgc cgcgcctct  cgccaccgcc aatccccga  ccaatcccaa tcccaatccc    60
catccccaca ccacaagcac caccaccacc accaaaccac ccgggccccc aagcccaagc   120
ccaagcccca gccaccgccg ccgcagcagc cgcgatctca gcctccgccg ccgccgcggc   180
accagcccca gcaggcgccc agcaggcgg cggcggagga tggggtgggg cgggtgctgg    240
ggcggcccat ggaggacgtc cgtgcgacct acaccttcgg gcgggagctg ggcgggggc    300 agttcggggt gacctacctc gccacccaca agcccaccgg ccgacgctac gcctgcaagt   360
ccatcgccgc ccgcaagctc gccgccccg acgacctcga cgacgtccgc cgcgaggtcc    420
acatcatgca ccacctcacc ggccaccgca acatcgtcga gctgcgcggc gcctacgagg   480
accgccactc cgtcaacctc gtcatggagc tctgcgaggg cggcgagctc ttcgaccgca   540
tcatcgccag gggccactac tccgagcgcg ccgccgccgc cctctgcagg gagatcgtct   600
ccgtcgtcca cagctgccac tccatggggg tcatgcacag ggacctcaag cccgagaact   660
```

```
tcctcttcct caacaagcgc gaggactccc cgctcaaagc caccgatttt ggcctctccg   720
tcttcttcaa gcccggtgag cagttcagag atcttgttgg aagtgcatat tatgtggctc   780
ctgaggtcct aaaacgacta tatggagctg aggcagacat atggagtgct ggagttatcc   840
tttacatcct tctatcaggg gttcctccat tctgggcaga aaacgaggac ggtatatttg   900
atgctgttct gcaaggtcat atcgacttct catctgaacc atggccttct atatctagtg   960
gtgcaaaaga cttggtcaag cggatgcttc ggcaggaccc aaaggagcgg ttaactgctg  1020
ctgaaatttt gaaccaccca tggattagag aggatggaga ggccccagat aaaccacttg  1080
atattacagt gatcagtaga atgaagcagt tcagagcaat gaacaaactt aagaaggttg  1140
ccttgaaggt cgttgcagag aacttgtcag aggaagagat tgtgggttta aaggaaatgt  1200
tcaaatcttt agatactgat aacagtggga cgataactct tgaagaacta agagctggtc  1260
taccaaagct tggcactaaa atttcggaat cagaattaag gcagttgatg gaagcggctg  1320
atgttgatgg aaatgggtcc attgattatg ttgaatttat atcagcaacg atgcacatga  1380
atagattaga aaggaagat cacatatata aagcatttga atattttgac aaggaccaca  1440
gcgggttcat aacagtcgat gaattggaag aagctctgac aaagtacgac atgggtgatg  1500
aagcgacaat taaagaaata attgctgaag tggatacaga ccatgatgga agaattaact  1560
accaggagtt tgttgccatg atgaagaaca acagccctga gattgttcca atcgacggc  1620
ggatgtttta agcctttcct acagttattg tgaagttttt ttcctttcac aaattctata  1680
tggttccatc ttagggaagt gagcattatc tttgtaaatg ttacaagagc agttcgtatc  1740
ggcggaattc aatgaagtat atgcaaggca tattggactc gttatgtatc atggtggata  1800
gctctctgaa gtgggtgtgg tgcgtttgtg tatgtatgct tgtgctttct ggccatatgt  1860
tttctgtctc ttgataaaaa gagctctgta aaacagtttc tactgatcat atcaggcaag  1920
gcaagataac gctttttc                                                1937
```

<210> SEQ ID NO 4
<211> LENGTH: 542
<212> TYPE: PRT
<213> ORGANISM: Oryza sativa

<400> SEQUENCE: 4

```
Met Gly Ala Arg Ala Ser Arg His Arg Gln Ser Pro Asp Gln Ser Gln
 1               5                  10                  15

Ser Gln Ser Pro Ser Pro His His Lys His His His His Gln Thr
            20                  25                  30

Thr Arg Ala Pro Lys Pro Lys Pro Lys Pro Gln Pro Pro Pro Gln
        35                  40                  45

Gln Pro Arg Ser Gln Pro Pro Pro Arg His Gln Pro Gln Gln
     50                  55                  60

Ala Pro Gln Gln Ala Ala Ala Glu Asp Gly Val Gly Arg Val Leu Gly
 65                  70                  75                  80

Arg Pro Met Glu Asp Val Arg Ala Thr Tyr Thr Phe Gly Arg Glu Leu
                 85                  90                  95

Gly Arg Gly Gln Phe Gly Val Thr Tyr Leu Ala Thr His Lys Pro Thr
            100                 105                 110

Gly Arg Arg Tyr Ala Cys Lys Ser Ile Ala Ala Arg Lys Leu Ala Arg
        115                 120                 125

Pro Asp Asp Leu Asp Asp Val Arg Glu Val His Ile Met His His
    130                 135                 140
```

Leu Thr Gly His Arg Asn Ile Val Glu Leu Arg Gly Ala Tyr Glu Asp
145                 150                 155                 160

Arg His Ser Val Asn Leu Val Met Glu Leu Cys Glu Gly Gly Glu Leu
            165                 170                 175

Phe Asp Arg Ile Ile Ala Arg Gly His Tyr Ser Glu Arg Ala Ala Ala
        180                 185                 190

Ala Leu Cys Arg Glu Ile Val Ser Val His Ser Cys His Ser Met
    195                 200                 205

Gly Val Met His Arg Asp Leu Lys Pro Glu Asn Phe Leu Phe Leu Asn
    210                 215                 220

Lys Arg Glu Asp Ser Pro Leu Lys Ala Thr Asp Phe Gly Leu Ser Val
225                 230                 235                 240

Phe Phe Lys Pro Gly Glu Gln Phe Arg Asp Leu Val Gly Ser Ala Tyr
            245                 250                 255

Tyr Val Ala Pro Glu Val Leu Lys Arg Leu Tyr Gly Ala Glu Ala Asp
        260                 265                 270

Ile Trp Ser Ala Gly Val Ile Leu Tyr Ile Leu Leu Ser Gly Val Pro
    275                 280                 285

Pro Phe Trp Ala Glu Asn Glu Asp Gly Ile Phe Asp Ala Val Leu Gln
290                 295                 300

Gly His Ile Asp Phe Ser Ser Glu Pro Trp Pro Ser Ile Ser Ser Gly
305                 310                 315                 320

Ala Lys Asp Leu Val Lys Arg Met Leu Arg Gln Asp Pro Lys Glu Arg
            325                 330                 335

Leu Thr Ala Ala Glu Ile Leu Asn His Pro Trp Ile Arg Glu Asp Gly
        340                 345                 350

Glu Ala Pro Asp Lys Pro Leu Asp Ile Thr Val Ile Ser Arg Met Lys
    355                 360                 365

Gln Phe Arg Ala Met Asn Lys Leu Lys Lys Val Ala Leu Lys Val Val
    370                 375                 380

Ala Glu Asn Leu Ser Glu Glu Ile Val Gly Leu Lys Glu Met Phe
385                 390                 395                 400

Lys Ser Leu Asp Thr Asp Asn Ser Gly Thr Ile Thr Leu Glu Glu Leu
            405                 410                 415

Arg Ala Gly Leu Pro Lys Leu Gly Thr Lys Ile Ser Glu Ser Glu Leu
        420                 425                 430

Arg Gln Leu Met Glu Ala Ala Asp Val Asp Gly Asn Gly Ser Ile Asp
    435                 440                 445

Tyr Val Glu Phe Ile Ser Ala Thr Met His Met Asn Arg Leu Glu Lys
450                 455                 460

Glu Asp His Ile Tyr Lys Ala Phe Glu Tyr Phe Asp Lys Asp His Ser
465                 470                 475                 480

Gly Phe Ile Thr Val Asp Glu Leu Glu Glu Ala Leu Thr Lys Tyr Asp
            485                 490                 495

Met Gly Asp Glu Ala Thr Ile Lys Glu Ile Ala Glu Val Asp Thr
        500                 505                 510

Asp His Asp Gly Arg Ile Asn Tyr Gln Glu Phe Val Ala Met Met Lys
    515                 520                 525

Asn Asn Ser Pro Glu Ile Val Pro Asn Arg Arg Arg Met Phe
    530                 535                 540

<210> SEQ ID NO 5
<211> LENGTH: 1578
<212> TYPE: DNA

<213> ORGANISM: Oryza sativa

<400> SEQUENCE: 5

```
gcgatggttg gcttcttctc ggtttgttcg ttccttgtgg tcgagagtga gtgaggtgga      60
ggagagagag gaggaggagg aggaggggat tcattcacgt ggcttccgga gagagcagga     120
gtcaacgtgc ggcttgactc tggagatctc tctctgtcgt ctcgcctcgc ccaaatcaga     180
agcgaatgat ggaggcgtcg aggtcgtgag agggagagga atcgacggag agagggaggc     240
ggcggcggcg gcaggaaggt tggagaagga gaggcagtgg agaagtcaag aacaagaacc     300
caatcaccga aacgcctcat cactgcagca atgccatcat caaccatggc cgtcgacacc     360
actgcttcgg agtactggct caattggagg ttcatgctct gcgcggtctg ggtctactcc     420
tgcatggtcc tggcatgctt cttgatctgg aagtacgagg ggccgagctc acaggacggc     480
aatggcgatg gcggcgagga cagtgaggat gcgcggccgc cccgggccgc atccggggtt     540
gtgtaccttg aagattgctg gaaaccatgc cttgagcaga tccacccctgg ctggctgctg     600
gcgttccgcg tcgtgtcttt cttcatttta gcctccctgc ttgcggttga tgtcgtcgtc     660
gatggatgga gtgtcttcct atactacact cagtggacct tcttgctagt caccttatat     720
tttgggcttg gttcggtgct ttcaatttat ggatgctatc agtattcata caagaatggc     780
gacaatagat ctggtgcaga tcatggcaca tatatcattg ctccagctgg ggaaagtgta     840
tatgatcagt caataaaaaa tccttgttac agtaaaatgc atggtggcaa agaaattgca     900
ggatttttggg gttatctgtt ccagatcatg tttcagacaa atgcaggtgc tgtgatgatt     960
acagatctgg tgttttggtt tatcctgtac cctttccttg cctacaatca atatgatatg    1020
aatttttttgc tgattgggac acactctata atgttgtgt tcatgattgg tgatactgct    1080
atgaatagcc tgcgtttccc gtggtttaga atcgcatatt tcttgctgtg gactggcgct    1140
tttgttaatg ttcagtggct catccatgct agcatatcga tttggtggcc ttacccattt    1200
ctggacttag catttcctaa agctcctgta tggtatttgg tggtagcagt gatgcatttc    1260
ccttgctatg ctttattcgc cctggttatg aggctaaaac aatctctgct ggaaagatgg    1320
tttcctcaga gttacacctg cgtgtagcaa acaagaacat atatagtgtt acaatttccc    1380
tcctgctgca tcctgcaaat gcaaattata tggagctgct gctcaccgta aattcctaga    1440
aaccatattg ttcagggtta gatgatattt cgtaaatttt tttcagacag cagcttcttt    1500
gagtcagctg ttgtctcctg ctctttttcaa tggagaaaac tgtacagtcc aatataataa    1560
tatatggcat tctcaacc                                                  1578
```

<210> SEQ ID NO 6
<211> LENGTH: 338
<212> TYPE: PRT
<213> ORGANISM: Oryza sativa

<400> SEQUENCE: 6

```
Met Pro Ser Ser Thr Met Ala Val Asp Thr Thr Ala Ser Glu Tyr Trp
 1               5                  10                  15

Leu Asn Trp Arg Phe Met Leu Cys Ala Val Trp Val Tyr Ser Cys Met
            20                  25                  30

Val Leu Ala Cys Phe Leu Ile Trp Lys Tyr Glu Gly Pro Ser Ser Gln
        35                  40                  45

Asp Gly Asn Gly Asp Gly Gly Glu Asp Ser Glu Asp Ala Arg Pro Pro
    50                  55                  60

Arg Ala Ala Ser Gly Val Val Tyr Leu Glu Asp Cys Trp Lys Pro Cys
```

```
                65                  70                  75                  80
Leu Glu Gln Ile His Pro Gly Trp Leu Leu Ala Phe Arg Val Val Ser
                        85                  90                  95
Phe Phe Ile Leu Ala Ser Leu Leu Ala Val Asp Val Val Asp Gly
                100                 105                 110
Trp Ser Val Phe Leu Tyr Tyr Thr Gln Trp Thr Phe Leu Leu Val Thr
                115                 120                 125
Leu Tyr Phe Gly Leu Gly Ser Val Leu Ser Ile Tyr Gly Cys Tyr Gln
            130                 135                 140
Tyr Ser Tyr Lys Asn Gly Asp Asn Arg Ser Gly Ala Asp His Gly Thr
145                 150                 155                 160
Tyr Ile Ile Ala Pro Ala Gly Glu Ser Val Tyr Asp Gln Ser Ile Lys
                165                 170                 175
Asn Pro Cys Tyr Ser Lys Met His Gly Gly Lys Glu Ile Ala Gly Phe
                180                 185                 190
Trp Gly Tyr Leu Phe Gln Ile Met Phe Gln Thr Asn Ala Gly Ala Val
            195                 200                 205
Met Ile Thr Asp Leu Val Phe Trp Phe Ile Leu Tyr Pro Phe Leu Ala
    210                 215                 220
Tyr Asn Gln Tyr Asp Met Asn Phe Leu Leu Ile Gly Thr His Ser Ile
225                 230                 235                 240
Asn Val Val Phe Met Ile Gly Asp Thr Ala Met Asn Ser Leu Arg Phe
                245                 250                 255
Pro Trp Phe Arg Ile Ala Tyr Phe Leu Leu Trp Thr Gly Ala Phe Val
                260                 265                 270
Asn Val Gln Trp Leu Ile His Ala Ser Ile Ser Ile Trp Trp Pro Tyr
            275                 280                 285
Pro Phe Leu Asp Leu Ala Phe Pro Lys Ala Pro Val Trp Tyr Leu Val
    290                 295                 300
Val Ala Val Met His Phe Pro Cys Tyr Ala Leu Phe Ala Leu Val Met
305                 310                 315                 320
Arg Leu Lys Gln Ser Leu Leu Glu Arg Trp Phe Pro Gln Ser Tyr Thr
                325                 330                 335
Cys Val

<210> SEQ ID NO 7
<211> LENGTH: 1704
<212> TYPE: DNA
<213> ORGANISM: Oryza sativa

<400> SEQUENCE: 7
gcctcgcgcc tcgcgagccg cgtccacctc cgcgcgggcg ccacgccacg ccacgcccac      60
ccaaacagct tcgctcgcct tcctcctctc ggccctcgcc gcgtccaccc cccccgatc     120 gagccgccct cccctccgc ctcccgcctc cgcgcgcgtt taggaggggg tcgggaggcc     180
cgaagctggg ccggcgtctc cgccccgcag ggtccgggaa ggagagatag ggagaagggt    240
cctcggctcc tcgcgccgcg tgctttggac tgggagtagc tggtgctaga agtaattttt    300
ggaaatggtt agtgggaggt cagcaaatgg ggaattggat gcatgcttca gaagcctcat    360
gctttcgatc agcagcggga gggggcaggc tgaaggtggt ggtgcaatgc caaccttgtc    420
aggctggaag gaccttccta ttgagctgct tctgcggatc atgtcgataa ttggagatga    480
ccggatgctt gtcgtggcat ccggtgtttg cactggctgg cgcgacgcgc tgggatgggg    540
gcttactaat ctttccctct cacggtgcca gcagaacatg aataacttaa tgatatcact    600
```

```
tgctcacaag ttcacgaagc ttcaagttct cactcttcgc cagaacatac ctcagcttga   660
agacagtgca gtagaggccg tttccaacta ctgtcatgat ctacgtgagt tagaccttag   720
cagaagtttt aggcttagtg accgttcctt gtatgcatta gcccgtggct gtcctcagct   780
tacaaaatta acattagtg gatgttccaa cttcagtgac actgccttga cctatcttac    840
tttccactgt aaaaatttta agtgcttgaa tctatgtggt tgtgggaagg cagcaaccga   900
cagagctttg caggccatag cccgtaattg cggccagctg caatcattga acttaggttg   960
gtgtgaggat gtcacagata agggagtgac cagcttggca tcagggtgtc ctgatctcag  1020
ggctctggac ttgtgtggtt gtgttcttat aacagatgag agtgtgatcg ctcttgccac  1080
tgggtgtcca cacctgcgat ctttaggctt gtactactgc cagaacatca ccgaccgagc  1140
catgtactcc ctcgcaaaca gccgggtcaa gagcaaacgc aggaggtggg acagtgtgag  1200
gagcagcagc tctaaggaag aagacggtct cgcaaacctg aacatcagcc agtgcacggc  1260
cctgacaccc ccagcggtcc aggcggtctg cgactccttc ccggccctcc acacttgccc  1320
tgggaggcac tccctgatca tcagtggctg cctcagcctg acgtctgtcc actgcgcctg  1380
cgccctccac ccgcaccgta ctggaagaac catggtgcct agccacgcat actgatggtg  1440
ttttgggcgc ttggtcctgg tgaatgccct attgcctggt ggatgatgag gtgttccttc  1500
ctggcctaga ggaagaagct gtgtgaataa actcagaact caaataatgt acagtaggac  1560
tctatatctg taggaatgat aaccatggag tggagaatgg ctggagagtt gcgtctcccc  1620
tgccattcag gccactgact gcaaactact acaaagatgt gtgtgtgtgt gctatgtagc  1680
ggacttctat taagtggctt gtct                                          1704
```

<210> SEQ ID NO 8
<211> LENGTH: 376
<212> TYPE: PRT
<213> ORGANISM: Oryza sativa

<400> SEQUENCE: 8

```
Met Val Ser Gly Arg Ser Ala Asn Gly Glu Leu Asp Ala Cys Phe Arg
1               5                   10                  15

Ser Leu Met Leu Ser Ile Ser Ser Gly Arg Gly Gln Ala Glu Gly Gly
            20                  25                  30

Gly Ala Met Pro Thr Leu Ser Gly Trp Lys Asp Leu Pro Ile Glu Leu
        35                  40                  45

Leu Leu Arg Ile Met Ser Ile Ile Gly Asp Asp Arg Met Leu Val Val
    50                  55                  60

Ala Ser Gly Val Cys Thr Gly Trp Arg Asp Ala Leu Gly Trp Gly Leu
65                  70                  75                  80

Thr Asn Leu Ser Leu Ser Arg Cys Gln Gln Asn Met Asn Asn Leu Met
                85                  90                  95

Ile Ser Leu Ala His Lys Phe Thr Lys Leu Gln Val Leu Thr Leu Arg
            100                 105                 110

Gln Asn Ile Pro Gln Leu Glu Asp Ser Ala Val Glu Ala Val Ser Asn
        115                 120                 125

Tyr Cys His Asp Leu Arg Glu Leu Asp Leu Ser Arg Ser Phe Arg Leu
    130                 135                 140

Ser Asp Arg Ser Leu Tyr Ala Leu Ala Arg Gly Cys Pro Gln Leu Thr
145                 150                 155                 160

Lys Leu Asn Ile Ser Gly Cys Ser Asn Phe Ser Asp Thr Ala Leu Thr
                165                 170                 175
```

```
Tyr Leu Thr Phe His Cys Lys Asn Phe Lys Cys Leu Asn Leu Cys Gly
            180                 185                 190

Cys Gly Lys Ala Ala Thr Asp Arg Ala Leu Gln Ala Ile Ala Arg Asn
        195                 200                 205

Cys Gly Gln Leu Gln Ser Leu Asn Leu Gly Trp Cys Glu Asp Val Thr
        210                 215                 220

Asp Lys Gly Val Thr Ser Leu Ala Ser Gly Cys Pro Asp Leu Arg Ala
225                 230                 235                 240

Leu Asp Leu Cys Gly Cys Val Leu Ile Thr Asp Glu Ser Val Ile Ala
                245                 250                 255

Leu Ala Thr Gly Cys Pro His Leu Arg Ser Leu Gly Leu Tyr Tyr Cys
            260                 265                 270

Gln Asn Ile Thr Asp Arg Ala Met Tyr Ser Leu Ala Asn Ser Arg Val
            275                 280                 285

Lys Ser Lys Arg Arg Arg Trp Asp Ser Val Arg Ser Ser Ser Ser Lys
        290                 295                 300

Glu Glu Asp Gly Leu Ala Asn Leu Asn Ile Ser Gln Cys Thr Ala Leu
305                 310                 315                 320

Thr Pro Pro Ala Val Gln Ala Val Cys Asp Ser Phe Pro Ala Leu His
                325                 330                 335

Thr Cys Pro Gly Arg His Ser Leu Ile Ile Ser Gly Cys Leu Ser Leu
            340                 345                 350

Thr Ser Val His Cys Ala Cys Ala Leu His Pro His Arg Thr Gly Arg
                355                 360                 365

Thr Met Val Pro Ser His Ala Tyr
        370                 375

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtacgtattt ttacaacaat taccaacaac                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggattcaatc ttaagaaact ttattgccaa                                    30
```